United States Patent [19]

Audiau et al.

[11] Patent Number: 4,535,080
[45] Date of Patent: Aug. 13, 1985

[54] DERIVATIVES OF 2-PIPERAZINO-PYRIMIDINE, METHODS FOR THEIR PREPARATION AND THEIR UTILIZATION AS DRUGS OR INTERMEDIATES FOR DRUGS

[75] Inventors: Francois Audiau, Charenton; Claude G. A. Gueremy, Houilles; Gérard R. Le Fur, Plessis Robinson, all of France

[73] Assignee: Pharmuka Laboratoires, Gennevilliers, France

[21] Appl. No.: 525,799

[22] Filed: Aug. 24, 1983

Related U.S. Application Data

[63] Continuation of Ser. No. 361,235, Mar. 24, 1982, abandoned.

[30] Foreign Application Priority Data

Apr. 7, 1981 [FR] France .................. 81 06924

[51] Int. Cl.³ .................. A61K 31/505; C07D 403/04
[52] U.S. Cl. .................. 514/255; 544/295; 544/298; 544/326; 544/330; 544/334; 544/335
[58] Field of Search .................. 544/295; 424/251

[56] References Cited

U.S. PATENT DOCUMENTS

| | | | |
|---|---|---|---|
| 2,543,972 | 11/1947 | Hultquist et al. | 544/295 |
| 3,435,036 | 3/1969 | Regnier et al. | 544/295 |
| 3,843,656 | 10/1974 | Obellianne et al. | 424/251 |
| 3,980,781 | 9/1976 | Snell et al. | 544/295 |
| 4,051,244 | 9/1977 | Mattioda et al. | 544/295 |
| 4,166,852 | 9/1979 | Loiseau et al. | 544/295 |

FOREIGN PATENT DOCUMENTS

| | | |
|---|---|---|
| 1620419 | 3/1972 | Fed. Rep. of Germany . |
| 2173746 | 10/1973 | France . |
| 2257294 | 8/1975 | France . |
| 2281117 | 3/1976 | France . |
| 2311776 | 12/1976 | France . |

OTHER PUBLICATIONS

Audiau, et al., "Chemical Abstracts", vol. 98, 1983, Col. 98: 89385y.

Primary Examiner—Glennon H. Hollrah
Assistant Examiner—James H. Turnipseed
Attorney, Agent, or Firm—Beveridge, DeGrandi & Weilacher

[57] ABSTRACT

Compounds are disclosed as useful as drugs or as intermediates for the manufacture of drugs, the compounds having the formula:

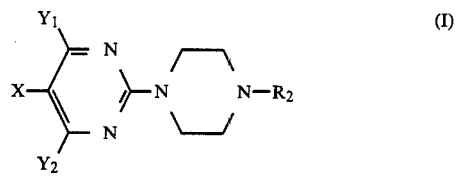

in which X is hydrogen, chlorine, alkyl, alkoxy or alkylthio having 1 to 3 carbon atoms, $R_2$ is hydrogen or alkyl having 1 to 3 carbon atoms, $Y_2$ is chlorine and $Y_1$ is chlorine or

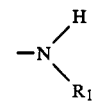

in which $R_1$ is hydrogen, straight or branched chain alkyl having 1 to 7 carbon atoms, cycloalkyl having 3 to 7 carbon atoms or cycloalkylalkyl having 4 to 8 carbon atoms, or $Y_2$ and $Y_1$ are both OH. Also disclosed are methods for preparation of the compounds.

8 Claims, No Drawings

DERIVATIVES OF 2-PIPERAZINO-PYRIMIDINE, METHODS FOR THEIR PREPARATION AND THEIR UTILIZATION AS DRUGS OR INTERMEDIATES FOR DRUGS

This application is a continuation of application Ser. No. 361,235, filed Mar. 24, 1982, now abandoned.

The present invention relates to derivatives of 2-piperazino-pyrimidine, methods for their preparation and their utilization either as intermediate products for the manufacture of drugs, or as antihypertension, hypoglycemic antimigraine, antidepressant drugs or as drugs for the treatment of senescence, Parkinson's disease or opium withdrawal symptoms.

Derivatives of 2-amino-6-chloro-4-piperazino-pyrimidine with antiemetic, antiserotonin, neuroleptic, analgesic and spasmolytic activities are already known (see, for example, French Pat. Nos. 2,173,746; 2,257,294; and 2,281,117; and G. Mattioda et Coll., J. Med. Chem. 18, 553, 1975).

The compounds according to the invention can be represented by the general formula:

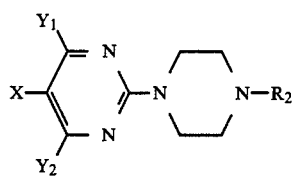
(I)

in which X is a hydrogen or a chlorine atom or an alkyl, alkoxy or alkylthio group having 1 to 3 carbon atoms, $R_2$ is a hydrogen atom or an alkyl group having 1 to 3 carbon atoms, $Y_2$ is a chlorine atom and $Y_1$ is a chlorine atom or an

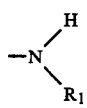

group in which $R_1$ is a hydrogen atom, a straight or branched chain alkyl group having 1 to 7 carbon atoms, a cycloalkyl group having 3 to 7 carbon atoms or a cycloalkylalkyl group having 4 to 8 carbon atoms, or else both $Y_2$ and $Y_1$ are OH groups.

In the above formula (I), when $Y_1$ is an

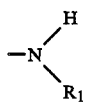

group, $R_1$ is preferably a branched chain alkyl group, in particular an isopropyl group.

The compounds of formula (I) in which $Y_1$ and $Y_2$ are OH groups can be prepared by condensation of a diester of the formula:

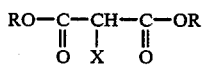
(II)

in which X has the same meaning as in formula (I) and R is an alkyl group of low molecular weight such as methyl or ethyl, with an amidine of the formula:

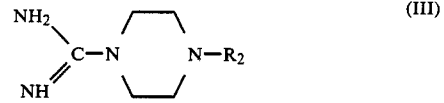
(III)

in which $R_2$ has the same meaning as in formula (I), according to the following reaction:

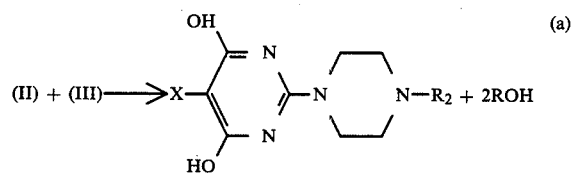
(a)

The above condensation reaction (a) can be carried out according to methods known per se (cf. for example "The Pyrimidines", Interscience Publishers, p. 51, 1962). It can be carried out in particular in methanol, at the reflux temperature of the solvent and in the presence of sodium methylate.

Compounds of formula (I) in which $Y_1$ and $Y_2$ are chlorine atoms can be prepared by the action of chlorinating agent on compounds of formula (I) in which $Y_1$ and $Y_2$ are OH groups. This reaction can be carried out according to methods known per se (cf. "The Pyrimidines", Interscience Publishers, p. 51, 1962). Phosphorus oxychloride can be mentioned in particular as a suitable chlorinating agent.

Compounds of formula (I) in which $Y_1$ and $Y_2$ are chlorine atoms and $R_2$ is an alkyl group having 1 to 3 carbon atoms can also be prepared by the condensation of 2,4,6-trichloropyrimidine of formula (IV), in which X has the same meaning as in formula (I), with a piperazine of formula (V) in which $R'_2$ is an alkyl group having 1 to 3 carbon atoms, according to the reaction represented as follows:

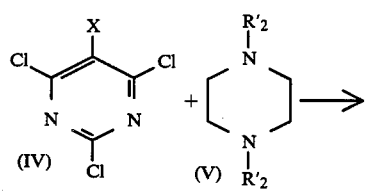

$R'_2Cl +$ 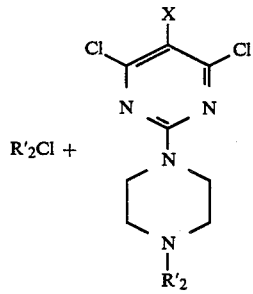

Condensation reaction (b) is carried out in accordance with methods known per se (cf. "The Pyrimidines", p. 345, 1962; ditto, Supplement I, p. 133, 1970). It can be carried out, for example, by heating compounds (IV) and (V) in an inert solvent such as an aromatic hydrocarbon (for example, toluene or xylene), at a temperature from 50° C. to 150° C.

Compounds of formula (I) in which $Y_1$ is a

group, $Y_2$ a chlorine atom and $R_2$ a hydrogen atom, can be prepared by the hydrolysis of N-acylated derivatives of the formula:

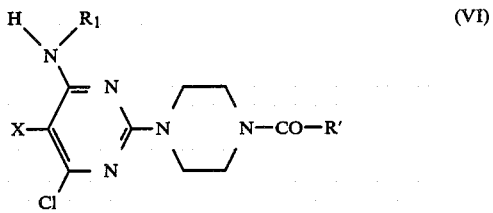

(VI)

in which X and $R_1$ have the same meaning as in formula (I) and R' is the hydrogen atom, an alkyl group of low molecular weight (for example, methyl) or a phenyl group. This hydrolysis can be carried out by heating compound (VI) in a solution of an inorganic acid such as hydrochloric acid or sulfuric acid in water or in a mixture of water and a solvent miscible with water (for example, methanol, ethanol, acetic acid, dioxan), at the reflux temperature of the medium.

N-acylated derivatives of formula (VI) can be prepared by condensation of a 2,4,6-trichloropyrimidine of formula (IV) with a piperazine of formula (VII) and condensation of the compound of formula (VIII) thereby obtained with a compound of formula $R_1NH_2$, in which $R_1$ has the same meaning as in formula (I), according to the reaction represented by:

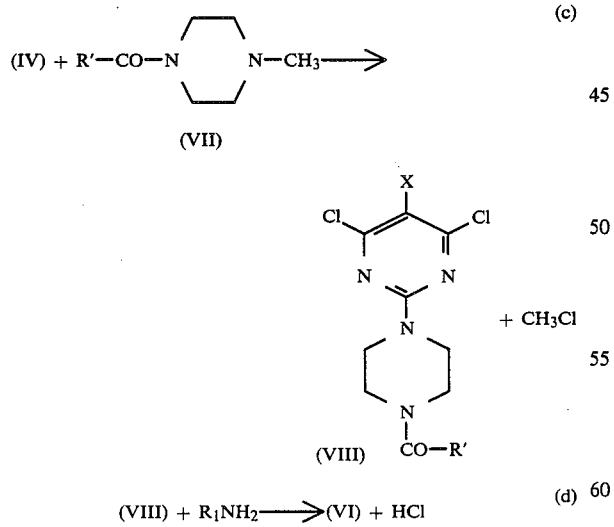

(c)

(VII)

(VIII)

(VIII) + $R_1NH_2 \longrightarrow$ (VI) + HCl   (d)

Condensation reaction (c) is carried out by heating compounds (IV) and (VII) in an inert solvent such as an aromatic hydrocarbon, for example, toluene or xylene, at a temperature between 50° C. and 150° C. Condensation reaction (d) is carried out under the same conditions as condensation reaction (e).

Compounds of formula (I) in which $Y_1$ is an

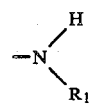

group, $Y_2$ a chlorine atom and $R_2$ an alkyl group, can be prepared by condensation of a compound of formula $R_1NH_2$, in which $R_1$ has the same meaning as in formula (I), with a compound of formula (IX), in which X has the same meaning as in formula (I) and $R'_2$ is an alkyl group having 1 to 3 carbon atoms, according to the following reaction:

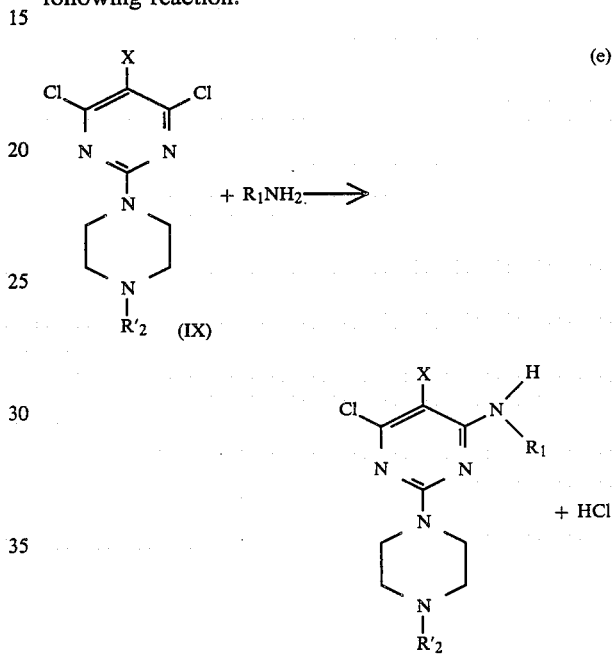

(e)

Condensation reaction (e) is carried out by heating compound (IX) and the compound $R_1NH_2$ at a temperature between 80° C. and 150° C. in a solvent and preferably in the presence of a base to fix the hydrochloric acid which is liberated. Among the solvents that can be used are included inert solvents such as hydrocarbons (for example, toluene, xylene), alcohols (for example, methanol, ethanol), ketones (for example, methylethylketone) and polar aprotic solvents (for example, dimethylformamide), or the $R_1NH_2$ compound in excess, when the latter is an amine. Bases which can be used include mineral bases such as potassium carbonate or an excess of the compound $R_1NH_2$ when it is ammonia, or organic bases such as an excess of compound $R_1NH_2$ when it is an amine. Depending on the solvent and the temperature used, condensation reaction (e) is carried out at a pressure equal to or greater than atmospheric pressure.

Compounds of formula (I) in which $Y_1$ is an

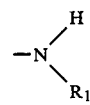

group, $Y_2$ a chlorine atom and $R_2$ an alkyl group, can also be prepared by the condensation of a piperazine of formula (X), in which $R'_2$ is an alkyl group having 1 to 3 carbon atoms, with a 2,6-dichloropyrimidine of formula (XI), in which X and $R_1$ have the same meaning as in formula (I), according to the following reaction:

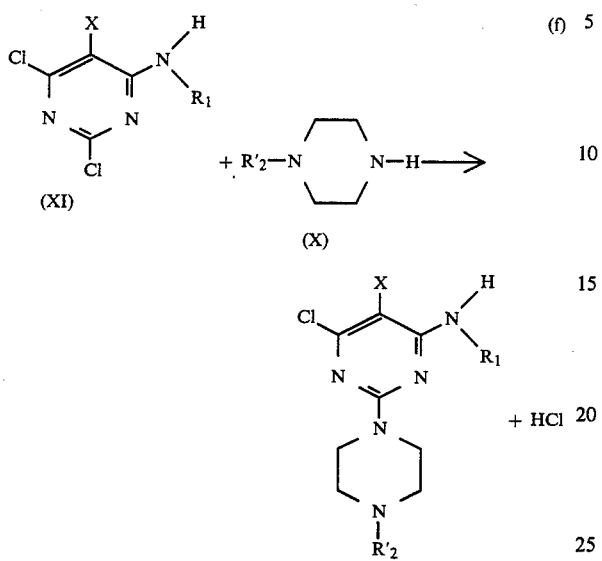

Condensation reaction (f) is carried out under conditions identical with those used for condensation reaction (e).

The 2,6-dichloropyrimidines of formula (XI) are obtained by condensation of a compound of the formula $R_1NH_2$, in which $R_1$ has the same meaning as in formula (I), with a 2,4,6-trichloropyrimidine of formula (IV). This condensation is carried out in an inert solvent such as those used for the reaction (e), for example, methylethylketone, in the presence of a mineral or organic base, for example triethylamine, at a temperature close to the ambient temperature. This generally gives a mixture of two position isomers, as is shown in the following reaction:

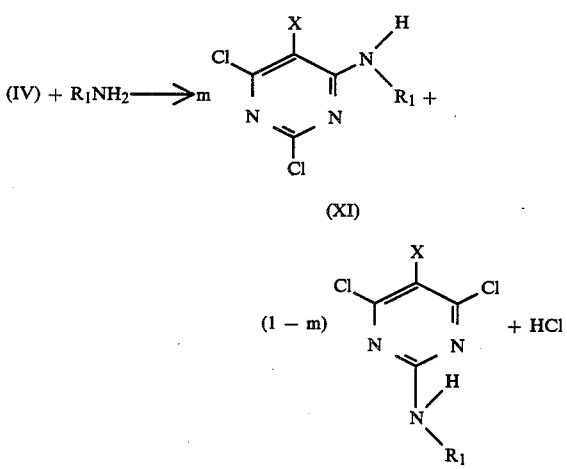

These two isomers can be separated from their mixture by conventional methods such as silica column chromatography or recrystallization from an appropriate solvent.

However, in the case where X is the methoxy group and when operating under the conditions defined above (solvent: methylethylketone; base: triethylamine; temperature close to ambient temperature), the condensation of (IV) with $R_1NH_2$ gives substantially only the required isomer, that is, compound (XI). The method of synthesizing compounds of formula (I) using reaction (f) is therefore particularly interesting in the case where $X=OCH_3$.

The reaction mixtures obtained by the various methods previously described are treated in accordance with conventional methods including physical methods (evaporation, extraction with a solvent, distillation, crystallization, chromatography, etc.) or chemical methods (formation of salt and regeneration of base, etc.) in order to isolate compound (I) in a pure state.

Compounds of formula (I) in the form of free base can be converted into addition salts with a mineral or organic acid by the action of such an acid in an appropriate solvent.

Compounds of formula (I) in which $Y_2$ is a chlorine atom and $Y_1$ is an

group have pharmacological properties. They do not have any antiemetic or neuroleptic activity, but have the property of binding to the alpha receptors of noradrenaline. Although they have a chemical structure far away from that of clonidine, they displace the latter from its binding sites. Clonidine behaves as an agonist towards alpha adrenergic receptors. In particular, it has a strong affinity for the category called alpha-2 of these receptors, a category which modulates, among others, the liberation of noradrenaline at the central level and at the peripheral level.

The following examples illustrate the invention without limiting it.

EXAMPLE 1

2-N-methylpiperazino-4,6-dihydroxypyrimidine 47.7 g of the acid sulfate of (1-methyl-4-piperazino) carboxamidine and a solution of sodium methylate obtained by the action of 11.5 g of sodium on 270 ml of methanol were heated under reflux for 30 minutes. 40 g of diethyl malonate were then added and heating under reflux was continued for 5 hours. After cooling, the reaction mixture was poured into water, and the resulting solution was neutralized with acetic acid and evaporated under reduced pressure. The residue was taken up with 1 liter of chloroform, the suspension thereby obtained was heated to boiling, and then cooled. The insoluble matter was drained and dried under reduced pressure. In this way, 70 g of a solid was obtained which consisted essentially of 2-N-methylpiperazino-4,6-dihydroxypyrimidine.

The (1-methyl-4-piperazino) carboxamidine was prepared as indicated by Stankevicius et Coll., Khim. Farm. Zh. 5 (1), 13–16 (1971).

EXAMPLE 2

2-N-methylpiperazino-4,6-dichloropyrimidine

The 2-N-methylpiperazino-4,6-dihydroxyprimidine obtained in Example 1 was reacted with 180 ml of phosphorus oxychloride, first at ambient temperature, and then at the reflux temperature for 3 hours. The reaction mixture was then poured onto ice and neutralized by the addition of sodium hydroxide. It was then extracted with chloroform and the chloroform phase was evaporated under reduced pressure. The residue obtained was fixed on a silica gel column and eluted with a 9/1 toluene-diethylamine mixture (9 parts by volume of toluene for 1 part by volume of diethylamine). In this way were obtained 8.4 g of 2-N-methylpiperazino-4,6- dichloropryimidine.

EXAMPLE 3

2-N-methylpiperazino-4-methylamino-6-chloropyrimidine

A mixture of 7 g of 2-N-methylpiperazino-4,6-dichloropryimidine, 140 ml of toluene, 30 ml of a 33% by weight solution of methylamine in ethanol and 2.1 g of finely ground potassium carbonate was heated under reflux for 32 hours. Then the reaction mixture was filtered, the filtrate was evaporated under reduced pressure, and the residue fixed on a silica gel column and eluted with a 9/1 toluene-diethylamine mixture. The fractions containing the required product were evaporated and the residue was dissolved in diethyl oxide. A solution of hydrochloric acid in diethyl oxide was added. The precipitate formed was recrystallized from ethanol. In this way were obtained 4.8 g of the dihydrochloride of 2-N-methylpiperazino-4-methylamino-6-chloropyrimidine, of which the melting point was above 260° C.

EXAMPLE 4

2-N-methylpiperazino-4-isopropylamino-6-chloropyrimidine

By replacing methylamine by isopropylamine in Example 3, the hydrochloride of 2-N-methylpiperazino-4-isopropylamino-6-chloropyrimidine, melting with decomposition at about 225° C., was obtained.

EXAMPLE 5

2-N-methylpiperazino-4-cyclopentylamino-6-chloropyrimidine

By replacing the methylamine of Example 3 by cyclopentylamine, the hydrochloride of 2-N-methylpiperazino-4-cyclopentylamino-6-chloropyrimidine melting at 264° C. was obtained.

EXAMPLE 6

2-N-methylpiperazino-5-chloro-4,6-dihydroxypyrimidine 57.3 g of the acid sulfate of (1-methyl-4-piperazino) carboxamidine and a solution of sodium methylate obtained by the action of 13.8 g of sodium on 320 ml of methanol were heated under reflux for 30 minutes. 61.2 g of diethyl chloromalonate were then added and the mixture was heated under reflux for 5 hours. After cooling, the reaction mixture was poured into water, the resulting solution was neutralized with acetic acid and evaporated under reduced pressure. The residue was taken up with 500 ml of hot methanol, the insoluble matter drained immediately, washed with 100 ml of methanol and dried under reduced pressure. In this way, 77 g of solid product were obtained consisting principally of 2-N-methylpiperazino-5-chloro-4,6-dihydroxy-pyrimidine.

EXAMPLE 7

2-N-methylpiperazino-4,5,6-trichloropyrimidine

The 2-N-methylpiperazino-5-chloro-4,6-dihydroxy pyrimidine obtained in Example 6 was reacted with 300 ml of phosphorus oxychloride, first at ambient temperature, then at the reflux temperature for 5 hours. The reaction mixture was then poured onto ice and neutralized by the addition of ammonia. It was then extracted with chloroform and the chloroform phase evaporated under reduced pressure. In this way, 27.6 g of crude 2-N-methylpiperazino-4,5,6-trichloropyrimidine were obtained.

EXAMPLE 8

2-N-methylpiperazino-4-amino-5,6-dichloropyrimidine 22 g of crude 2-N-methylpiperazino-4,5,6-trichloropyrimidine obtained as indicated in Example 7 and a solution of 42 g of ammonia in 250 ml of methanol were heated at 130° C. for 3 hours in an autoclave. Then the reaction mixture was evaporated under reduced pressure, the residue was fixed on a silica gel column and eluted with a 95/5 chloroform-diethylamine mixture. In this way were obtained 11.3 g of 2-N-methylpiperazino-4-amino-5,6-dichloropyrimidine, of which the hydrochloride melted at 260° C.

EXAMPLE 9

2-N-methylpiperazino-4-methylamino-5,6-dichloropyrimidine 14 g of 2-N-methylpiperazino-4,5,6-trichloropyrimidine, 250 ml of toluene, 10 ml of a 33% by weight solution of methylamine in alcohol and 3.5 g of potassium carbonate were heated under reflux for 8 hours. This was followed by washing the reaction mixture with water and evaporating it under reduced pressure. The residue obtained was fixed on a silica gel column and eluted with a 9/1 toluene-diethylamine mixture. In this way were obtained 11.9 g of 2-N-methylpiperazino-4-methylamino-5,6-dichloropyrimidine, of which the hydrochloride melted above 260° C.

EXAMPLE 10

2-N-methylpiperazino-4-isopropylamino-5,6-dichloropyrimidine

The procedure followed was as in Example 9, starting with 10 g of 2-N-methylpiperazino-4,5,6-trichloropyrimidine instead of 14 g, and 7.2 ml of isopropylamine instead of the methylamine solution. In this way were obtained 8.8 g of 2-N-methylpiperazino-4-isopropylamino-5,6-dichloropyrimidine of which the hydrochloride melted at 252° C.

EXAMPLE 11

2-N-methylpiperazino-4-cyclopentylamino-5,6-dichloropyrimidine

The procedure followed was as in Example 9, starting with 22.5 g of 2-N-methylpiperazino-4,5,6-trichloropyrimidine instead of 14 g and 25 ml of cyclopentylamine instead of the methylamine solution. In this way were obtained 13.8 g of 2-N-methylpiperazino-4-cyclopentylamino-5,6-dichloropyrimidine, of which the hydrochloride melted at 258° C.

EXAMPLE 12

2-N-methylpiperazino-4-isopropylamino-5-methoxy-6-chloropyrimidine 42 ml of triethylamine, 25 ml of isopropylamine, 250 ml of methylethylketone and 32 g of 2,4,6-trichloro-5-methoxypyrimidine (prepared as indicated by Budesinsky et Coll., Ceskoslov. Farm. 10, 241–247, 1961) were stirred together at 20° C. for 6 hours. The reaction mixture was then evaporated under reduced pressure and the residue fixed on a silica gel column. This was followed by elution with a 95/5 toluene-diethylamine mixture. In this way were isolated 20.2 g of 4-isopropylamino-2,6-dichloro-5-methoxypyrimidine.

A mixture of 12 g 4-isopropylamino-2,6-dichloro-5-methoxypyrimidine, 250 ml of toluene, 12 ml of N-methylpiperazine and 3.5 g of potassium carbonate was heated under reflux for 8 hours. This was followed by washing the reaction mixture with water and evaporating the organic phase under reduced pressure. The residue obtained was fixed onto a silica gel column and eluted with a 9/1 toluene-diethylamine mixture. In this way were obtained 10.6 g of 2-N-methylpiperazino-4-isopropylamino-5-methoxy-6-chloropyrimidine, of which the hydrochloride melted at 142° C.

EXAMPLE 13

2-N-methylpiperazino-4,6-dihydroxy-5-methoxypyrimidine

The procedure followed was as in Example 6, starting with 57.3 g of the acid sulfate of (1-methyl-4-piperazino) carboxamidine and 48.6 g of dimethyl methoxymalonate. In this way was obtained 2-N-methylpiperazino-4,6-dihydroxy-5-methoxypyrimidine.

EXAMPLE 14

2-N-methylpiperazino-4,6-dichloro-5-methoxypyrimidine

The procedure followed was as in Example 7 by replacing at the start the 2-N-methylpiperazino-5-chloro-4,6-dihydroxypyrimidine by the 2-N-methylpiperazino-5-methoxy-4,6-dihydroxypyrimidine previously obtained. In this way were obtained 20.9 g of 2-N-methylpiperazino-4,6-dichloro-5-methoxypyrimidine.

EXAMPLE 15

2-N-methylpiperazino-4-cyclopentylamino-5-methoxy-6-chloropyrimidine 19.4 g of 2-N-methylpiperazino-4,6-dichloro-5-methoxypyrimidine, 300 ml of toluene, 16 ml of cyclopentylamine and 11 g of potassium carbonate were heated under reflux for 8 hours. This was followed by washing the reaction mixture with water and evaporating it under reduced pressure. The residue obtained was fixed on a silica gel column and eluted with an 85/15 toluene-methanol mixture. In this way were obtained 13.3 g of 2-N-methylpiperazino-4-cyclopentylamino-5-methoxy-6-chloropyrimidine, of which the hydrochloride melted above 260° C.

EXAMPLE 16

2-N-methylpiperazino-5-ethoxy-4,6-dihydroxypyrimidine

The procedure followed was as in Example 6, starting with 96 g of the acid sulfate of (1-methyl-4-piperazino) carboxamidine and 102 g of diethylethoxymalonate. In this way was obtained 2-N-methylpiperazino-5-ethoxy-4,6-dihydroxypyrimidine.

EXAMPLE 17

2-N-methylpiperazino-5-ethoxy-4,6-dichloropyrimidine

The procedure followed was as in Example 7 replacing at the start the 2-N-methylpiperazino-5-chloro-4,6-dihydroxypyrimidine by the 2-N-methylpiperazino-5-ethoxy-4,6-dihydroxypyrimidine previously obtained. In this was were obtained 28 g of 2-N-methylpiperazino-4,6-dichloro-5-ethoxypyrimidine.

EXAMPLE 18

2-N-methylpiperazino-4-isopropylamino-5-ethoxy-6-chloropyrimidine 14.55 g of 2-N-methylpiperazino-5-ethoxy-4,6-dichloropyrimidine, 250 ml of methylethylketone and 12.7 ml of isopropylamine were heated under reflux for 26 hours. The reaction mixture was then evaporated under reduced pressure and the residue obtained fixed on a silica gel column. This was followed by elution with a 95/5 chloroform-methanol mixture. In this way were obtained 11.4 g of 2-N-methylpiperazino-4-isopropylamino-5-ethoxy-6-chloropyrimidine, of which the hydrochloride melted at 174° C.

EXAMPLE 19

2-N-methylpiperazino-5-methyl-4,6-dihydroxypyrimidine

The procedure followed was as in Example 6, starting with 96 g of the acid sulfate of (1-methyl-4-piperazino) carboxamidine and 87 g of diethyl methylmalonate. In this way was obtained 2-N-methylpiperazino-5-methyl-4,6-dihydroxypyrimidine.

EXAMPLE 20

2-N-methylpiperazino-5-methyl-4,6-dichloropyrimidine

The procedure followed was as in Example 7, replacing at the start the 2-N-methylpiperazino-5-chloro-4,6-dihydroxypyrimidine by the 2-N-methylpiperazino-5-methyl-4,6- dihydroxypyrimidine previously obtained. In this way were obtained 97.8 g of 2-N-methylpiperazino-5-methyl-4,6-dichloropyrimidine.

EXAMPLE 21

2-N-methylpiperazino-4-isopropylamino-5-methyl-6-chloropyrimidine 21 g of 2-N-methylpiperazino-4,6-dichloro-5-methylpyrimidine, 300 ml of methylethylketone and 20.4 ml of isopropylamine were heated under reflux for 48 hours. The reaction mixture was evaporated under reduced pressure, and the residue fixed on a silica gel column. This was followed by elution with a 95/5 chloroform-methanol mixture. In this way were obtained 9.1 g of 2-N-methylpiperazino-4-isopropylamino-5-methyl-6-chloropyrimidine, of which the dihydrochloride melted at 258° C.

EXAMPLE 22

2-N-methylpiperazino-4-cyclopentylamino-5-methyl-6-chloropyrimidine 13 g of 2-N-methylpiperazino-5-methyl-4,6-dichloropyrimidine, 250 ml of toluene, 11.2 ml of cyclopentylamine and 7.7 g of potassium carbonate were heated under reflux for 48 hours. The reaction mixture was washed with water and then evaporated under reduced pressure. The residue obtained was fixed on a silica gel column and eluted with an 85/15 toluene-methanol mixture. In this way were obtained 14.2 g of 2-N-methylpiperazino-4-cyclopentylamino-5-methyl-6-chloropyrimidine, of which the hydrochloride melted at 260° C.

EXAMPLE 23

2-N-methylpiperazino-5-ethyl-4,6-dihydroxypyrimidine

The procedure followed was as in Example 6 starting with 96 g of the acid sulfate of (1-methyl-4-piperazino) carboxamidine and 99 g of diethyl ethylmalonate. In this way was obtained 2-N-methylpiperazino-5-ethyl-4,6-dihydroxypyrimidine.

EXAMPLE 24

2-N-methylpiperazino-5-ethyl-4,6-dichloropyrimidine

The procedure followed was as in Example 7, replacing at the start the 2-N-methylpiperazino-5-chloro-4,6-dihydroxypyrimidine by the 2-N-methylpiperazino-5-ethyl-4,6-dihydroxypyrimidine previously obtained. In this way were obtained 67.6 g of 2-N-methylpiperazino-5-ethyl-4,6-dichloropyrimidine.

EXAMPLE 25

2-N-methylpiperazino-4-isopropylamino-5-ethyl-6-chloropyrimidine

The procedure followed was as in Example 21 starting with 22 g of 2-N-methylpiperazino-5-ethyl-4,6-dichloropyrimidine. 300 ml of methylethylketone and 20.4 ml of isopropylamine. In this way, 6.7 g of 2-N-methylpiperazino-4-isopropylamino-5-ethyl-6-chloropyrimidine, of which the hydrochloride melted at 198° C., were obtained.

EXAMPLE 26

2-Piperazino-4-isopropylamino-5-methyl-6-chloropyrimidine (1) To a solution of 32 g of 1-methyl-4-formylpiperazine, prepared as indicated by J. Pharm. Soc. Japan, 74, 1049–1051, (1954), in 250 ml of toluene, maintained at 80° C., was added a solution of 49.4 g of 2,4,6-trichloro-5-methylpyrimidine (prepared as indicated in Pharm. Bull. 1, 387–390, 1953) in 250 ml of toluene. The reaction mixture was heated for 4 hours at a temperature of 80° C.–85° C., and then for 2 hours under reflux. The reaction mixture was then filtrated, the filtrate evaporated under reduced pressure and the residue fixed on a silica gel column. By elution with a 9/1 toluene-methanol mixture were obtained 26.3 g of 2-N-formyl-piperazino-4,6-dichloro-5-methylpyrimidine.

(2) To 26.3 g of this last product were added 250 ml of toluene and 30 ml of isopropylamine. The mixture was heated under reflux for 48 hours. The organic phase was washed with water, and then evaporated under reduced pressure. The residue was fixed on a silica gel column and eluted with a 95/5 toluene-methanol mixture. In this way were obtained 14 g of 2-N-formyl-piperazino-4-isopropylamino-5-methyl-6-chloropyrimidine, which melted at 164° C.

(3) 14 g of 2-N-formylpiperazino-4-isopropylamino-5-methyl-6-chloropyrimidine, 400 ml of water and 40 ml of concentrated hydrochloric acid were heated under reflux for 2 hours. The solution was then treated with 2 g of animal black, filtered, made alkaline by the addition of sodium hydroxide and extracted with chloroform. The chloroform phase was evaporated under reduced pressure and the residue dissolved in ethanol. A solution of hydrochloric acid in ethanol was then added. The precipitate formed was recrystallized twice from water. In this way were obtained 6.4 g of the hydrochloride of 2-piperazino-4-isopropylamino-5-methyl-6-chloropyrimidine, which melted at 199° C.

EXAMPLE 27

2-Piperazino-4-isopropylamino-5-methylthio-6-chloropyrimidine (1) By proceeding as in part (1) of Example 26, starting with 42.3 g of 1-methyl-4-formylpiperazine and 69 g of 2,4,6-trichloro-5-methylthiopyrimidine, 94.3 g of 2-N-formylpiperazino-4,6-dichloro-5-methylthiopyrimidine were obtained.

(2) To 94.3 g of this last product were added 700 ml of toluene, 52 ml of triethylamine and 30 ml of isopropylamine, and the mixture was heated at 100° C. for 4 hours. After hot filtration, the filtrate was washed with water and concentrated by distillation under reduced pressure. The residue was fixed on a silica gel column and eluted with a 95/5 toluene-diethylamine mixture. In this way were obtained 86 g of 2-N-formyl-piperazino-4-isopropylamino-5-methylthio-6-chloropyrimidine. After two recrystallizations from a 50/50 water-ethanol mixture, the product obtained had a melting point of 92° C.

(3) The procedure followed was as in part (3) of Example 26, replacing the 14 g of 2-N-formyl-piperazino-4-isopropylamino-5-methyl-6-chloropyrimidine by 80 g of 2-N-formylpiperazino-4-isopropylamino-5-methylthio-6-chloropyrimidine. After 3 recrystallizations from water of the hydrochloride formed in the ethanol, 30.5 g of the hydrochloride of 2-piperazino-4-isopropylamino-5-methylthio-6-chloropyrimidine, which melted at 147° C., were obtained.

EXAMPLE 28

2-N-methylpiperazino-4,6-dichloro-5-methylthiopyrimidine

To a solution of 38 g of N,N′-dimethylpiperazine in 300 ml of toluene was added, within a period of 1 hour at a temperature of about 100° C., a solution of 69 g of 2,4,6-trichloro-5-methylthiopyrimidine in 300 ml of toluene. The mixture was heated for two hours at 90° C., then cooled and filtered. The filtrate was concentrated by distillation under reduced pressure. The residue obtained was fixed onto a silica gel column and eluted with an 87/13 toluene-methanol mixture. In this way were obtained 69 g of 2-N-methylpiperazino-4,6-dichloro-5-methylthiopyrimidine, which melted at 80° C.

EXAMPLE 29

2-N-methylpiperazino-4-amino-5-methylthio-6-chloropyrimidine

A solution of 30 g of 2-N-methylpiperazino-4,6-dichloro-5-methylthiopyrimidine in 330 ml of methanol containing 60 g of ammonia was heated in an autoclave at 130° C. for 3 hours. Then the mixture was evaporated under reduced pressure and the residue fixed onto a silica gel column. This was followed by elution with a 98/2 chloroform-diethylamine mixture. In this way were obtained 10 g of 2-N-methylpiperazino-4-amino-5-methylthio-6-chloropyrimidine, which melted at 131° C.

EXAMPLE 30

2-N-methylpiperazino-4-isopropylamino-5-methylthio-6-chloropyrimidine

A solution of 2-N-methylpiperazino-4,6-dichloro-5-methylthiopyrimidine in toluene containing isopropylamine (this latter being present in excess, that is, the molar ratio isopropylamine/2-N-methylpiperazino-4,6-dichloro-5-methylthiopyrimidine is greater than (1) was heated under reflux for 16 hours. The reaction mixture was then treated as indicated in Example 29. In this way was obtained 2-N-methylpiperazino-4-isopropylamino-5-methylthio-6-chloropyrimidine, which melted at 68° C.

EXAMPLE 31

2-N-methylpiperazino-4-sec-butylamino-5-methylthio-6-chloropyrimidine

The procedure followed was as in Example 30, starting with 23.5 g of 2-N-methylpiperazino-4,6-dichloro-5-methylthiopyrimidine and 25 ml of sec-butylamine (instead of isopropylamine). In this way were obtained 20 g of 2-N-methylpiperazino-4-sec-butylamino-5-methylthio-6-chloropyrimidine. This last compound, subjected to the action of gaseous hydrochloric acid in diethyl oxide, gave a salt which was an equimolecular mixture of the monohydrochloride and the dihydrochloride melting at 186° C.

EXAMPLE 32

2-N-methylpiperazino-4-tert-butylamino-5-methylthio-6-chloropyrimidine 11.7 g of 2-N-methylpiperazino-4,6-dichloro-5-methylthiopyrimidine and 24 ml of tert-butylamine in methylethylketone were heated under reflux for 28 hours. The reaction mixture was then treated as indicated in Example 29. In this way were obtained 11.9 g of 2-N-methylpiperazino-4-tert-butylamino-5-methylthio-6-chloropyrimidine, of which the hydrochloride melted at 246° C.

EXAMPLE 33

2-N-methylpiperazino-4-cyclopropylamino-5-methylthio-6-chloropyrimidine

The procedure followed was as in Example 30, starting with 11.7 g of 2-N-methylpiperazino-4,6-dichloro-5-methylthiopyrimidine and 11.2 ml of cyclopropylamine (instead of isopropylamine). In this way were obtained 9.9 g of 2-N-methylpiperazino-4-cyclopropylamino-5-methylthio-6-chloropyrimidine, of which the hydrochloride melted at 232° C.

EXAMPLE 34

2-N-methylpiperazino-4-cyclopropylmethylamino-5-methylthio-6-chloropyrimidine

The procedure followed was as in Example 30, starting with 11.7 g of 2-N-methylpiperazino-4,6-dichloro-5-methylthiopryimidine and 3.1 g of cycloproplymethylamine. In this way were obtained 7.6 g of 2-N-methyl-piperazino-4-cyclopropylmethylamino-5-methylthio-6-chloropyrimidine, of which the hydrochloride melted at 211° C.

EXAMPLE 35

2-N-methylpiperazino-4-cyclobutylamino-5-methylthio-6-chloropyrimidine

The procedure followed was as in Example 30, starting with 11.7 g of 2-N-methylpiperazino-4,6-dichloro-5-methylthiopyrimidine and 3.1 g of cyclobutylamine. In this way were obtained 10.4 g of 2-N-methylpiperazino-4-cyclobutylamino-5-methylthio-6-chloro-pyrimidine, of which the hydrochloride melted at 226° C.

EXAMPLE 36

2-N-methylpiperazino-4-cyclopentylamino-5-methylthio-6-chloropyrimidine

The procedure followed was as in Example 30, starting with 11.7 g of 2-N-methylpiperazino-4,6-dichloro-5-methylthiopyrimidine and 15 ml of cyclopentylamine. In this way were obtained 11.1 g of 2-N-methylpiperazino-4-cyclopentylamino-5-methylthio-6-chloropyrimidine, of which the hydrochloride melted at 202° C.

EXAMPLE 37

2-N-methylpiperazino-4-cyclohexylamino-5-methylthio-6-chloropyrimidine

The procedure followed was as in Example 30, starting with 11.7 g of 2-N-methylpiperazino-4,6-dichloro-5-methylthiopyrimidine and 5.5 ml of cyclohexylamine (instead of isopropylamine). The 2-N-methylpiperazino-4-cyclohexylamino-5-methylthio-6-chloropyrimidine thereby obtained was converted into its hydrochloride by the action of hydrochloric acid in diethyl oxide. After two recrystallizations of this latter product from water, were obtained 7.7 g of the hydrochloride of 2-N-methylpiperazino-4-cyclohexylamino-5-methylthio-6-chloropyrimidine, which melted at 202° C.

PHARMACOLOGICAL PROPERTIES

Affinity for the Receptor Sites of Clonidine

This affinity was measured on rat cortex membranes according to the method of Greenberg D. A. et Coll., Life Sciences, 19, 69 (1976). It is expressed by a value $K_i$, in nanomoles (nM), which is obtained from the formula:

$$K_i = IC_{50} \left[ \frac{1}{1 + \frac{C}{K_D}} \right]$$

in which C represents the $^3$H clonidine concentration, $K_D$ an affinity constant characteristic of clonidine and $IC_{50}$ the concentration of product in nanomoles required to obtain a 50% inhibition of the binding of the $^3$H clonidine.

The results obtained are summarized in the following table in which are also included, for purposes of comparison, those given by two reference products (Yohimbine and Mianserine).

| Product | $K_i$ (nM) |
| --- | --- |
| Example 8 | 51 |
| Example 9 | 44 |
| Example 10 | 5 |
| Example 12 | 51 |
| Example 21 | 16 |

-continued

| Product | $K_i$ (nM) |
|---|---|
| Example 25 | 51 |
| Example 27 | 36 |
| Example 30 | 26 |
| Example 35 | 51 |
| Example 36 | 22 |
| Yohimbine | 45 |
| Mianserine | 30 |

Toxicological Properties

The acute toxicities of the compounds of formula (I) in which $$Y_2 = Cl \text{ and } Y_1 = N\begin{matrix}H\\R_1\end{matrix}$$

were determined for the male mouse $CD_1$ (Charles River) by oral administration. The $LD_{50}$ figures (50% lethal doses) were calculated, after three days observation, by the cumulative method of J. J. Reed and H. Muench (Amer. J. Hyg. 1938, 27, 493).

The compounds have a relatively low toxicity to mice, since their $LD_{50}$ are between 200 and 1000 mg/kg.

Therapeutic Utilization

The compounds of formula (I) in which $$Y_2 \text{ is } = Cl \text{ and } Y_1 \text{ is } -N\begin{matrix}H\\R_1\end{matrix}$$

and their salts with a pharmaceutically acceptable acid can be used in human therapy as the active substance of antihypertension hypoglycemic antimigraine and antidepressant drugs and of drugs for the treatment of senescence, Parkinson's disease or opium withdrawal symptoms. Said drugs contain, in addition to the active substance, a liquid or solid pharmaceutically acceptable carrier and may be in the form of tablets, capsules, losenges, suppositories, ingestible or injectable solutions, etc.

The dosage depends on the effects desired and the mode of administration. For example, by oral administration, the dosage can be between 10 and 500 mg of active substance per day, with unit doses ranging from 2 to 100 mg.

What is claimed is:

1. A drug, particularly useful as an antihypertension, hypoglycemic, antimigraine or antidepressant drug which contains a pharmaceutically acceptable carrier and, as the active principle, an effective amount of a compound of the formula:

$$\begin{matrix}Y_1\\X-\\Y_2\end{matrix}\begin{matrix}N\\\\N\end{matrix}-N\begin{matrix}\\\\\end{matrix}N-R_2 \quad (I)$$

in which X is hydrogen, chlorine, alkyl, alkoxy or alkylthio wherein the alkyl has from 1 to 3 carbon atoms, $R_2$ is hydrogen or alkyl having 1 to 3 carbon atoms, $Y_2$ is chlorine and $Y_1$ is $$-N\begin{matrix}H\\R_1\end{matrix}$$

in which $R_1$ is hydrogen or straight or branched chain alkyl having 1 to 7 carbon atoms, cycloalkyl having 3 to 7 carbon atoms or cycloalkylalkyl having 4 to 8 carbon atoms or a salt of said compound with a pharmaceutically acceptable acid.

2. The drug according to claim 1 wherein the active principle is the compound 2-piperazino-4-isopropylamino-6-chloro-5-methylthiopyrimidine or a salt of said compound with a pharmaceutically acceptable acid.

3. The drug according to claim 1 wherein the active principle is the compound 2-N-methylpiperazino-4-isopropylamino-5,6-dichloropyrimidine or a salt of said compound with a pharmaceutically acceptable acid.

4. The drug according to claim 1 wherein the active principle is the compound 2-N-methylpiperazino-4-isopropylamino-6-chloro-5-methoxypyrimidine or a salt of said compound with a pharmaceutically acceptable acid.

5. The drug according to claim 1 wherein the active principle is the compound 2-N-methylpiperazino-4-isopropylamino-6-chloro-5-methylpyrimidine or a salt of said compound with a pharmaceutically acceptable acid.

6. The drug according to claim 1 which contains 2 to 100 mg of active substance per unitary dose.

7. A method for the treatment of a warm blooded mammal afflicted with hyperglycemia, which comprises administering to said mammal a therapeutically effective amount of a compound of the formula:

$$\begin{matrix}Y_1\\X-\\Y_2\end{matrix}\begin{matrix}N\\\\N\end{matrix}-N\begin{matrix}\\\\\end{matrix}N-R_2 \quad (I)$$

in which X is hydrogen, chlorine, alkyl, alkoxy or alkylthio wherein the alkyl has from 1 to 3 carbon atoms, $R_2$ is hydrogen or alkyl having 1 to 3 carbon atoms, $Y_2$ is chlorine and $Y_1$ is $$-N\begin{matrix}H\\R_1\end{matrix}$$

in which $R_1$ is hydrogen or straight or branched chain alkyl having 1 to 7 carbon atoms, cycloalkyl having 3 to 7 carbon atoms or cycloalkylalkyl having 4 to 8 carbon atoms or a salt thereof with a pharmaceutically acceptable acid.

8. The drug according to claim 1, wherein the active principle is the compound 2-piperazino-4-isopropylamino-5-methyl-6-chloropyrimidine or a salt of said compound with a pharmaceutically acceptable acid.

* * * * *